US006618612B1

(12) United States Patent
Acker et al.

(10) Patent No.: US 6,618,612 B1
(45) Date of Patent: *Sep. 9, 2003

(54) INDEPENDENTLY POSITIONABLE TRANSDUCERS FOR LOCATION SYSTEM

(75) Inventors: David E. Acker, Setauket; Robert Pacheco, Kew Gardens; Yong Zou, Coram, all of NY (US); Yoel Zilberstein, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/125,080
(22) PCT Filed: Feb. 14, 1997
(86) PCT No.: PCT/US97/02650
§ 371 (c)(1),
(2), (4) Date: Feb. 16, 1999
(87) PCT Pub. No.: WO97/29685
PCT Pub. Date: Aug. 21, 1997

Related U.S. Application Data

(60) Provisional application No. 60/011,720, filed on Feb. 15, 1996, and provisional application No. 60/012,241, filed on Feb. 26, 1996.

(51) Int. Cl.[7] ............................................. A61B 5/00
(52) U.S. Cl. ................. 600/424; 600/427; 128/899
(58) Field of Search ................. 600/424, 427, 600/117, 429; 128/899; 606/130

(56) References Cited

U.S. PATENT DOCUMENTS

| | | | |
|---|---|---|---|
| 3,644,825 A | 2/1972 | Davis, Jr. et al. | 324/41 |
| 3,868,565 A | 2/1975 | Kuipers | 324/34 R |
| 4,017,858 A | 4/1977 | Kuipers | 343/100 R |
| 4,054,881 A | 10/1977 | Raab | 343/112 R |
| 4,176,662 A | 12/1979 | Frazer | |
| 4,560,930 A | 12/1985 | Kuono | 324/207 |
| 4,570,354 A | 2/1986 | Hindes | 33/534 |

(List continued on next page.)

FOREIGN PATENT DOCUMENTS

| | | |
|---|---|---|
| EP | 0 399 536 A | 11/1990 |
| EP | 0 419 729 A | 4/1998 |
| WO | WO 94/00050 | 1/1994 |
| WO | WO 94/04938 | 3/1994 |
| WO | WO 94/06349 | 3/1994 |

(List continued on next page.)

OTHER PUBLICATIONS

"Effects of laser irradiation delivered by flexible fiberoptic system on the left ventricular internal myocardium" American Heart Journal, Sep. 1983, pp. 587–590.
Dorothy Bonn, "High–Power laser help the Ischaemic Heart", The Lancet, vol. 348 (Jul. 13, 1996). p. 118.
Mahmood Mirhoseini et al. "Transmyocardial Laser Revascularization: A Review" Journal Of Clinical Laser Medicine & Surgery. vol. 11(1993) pp. 5–19.
Supplementary European Search Report 97906698–2–2305–US9702850 dated Mar. 12, 1999.

*Primary Examiner*—Ruth S. Smith
(74) *Attorney, Agent, or Firm*—Louis J. Capezzuto (57) ABSTRACT

A system for determining the disposition of a probe within the body of a patient includes a probe having probe field transducers and a plurality of reference field transducers. The reference field transducers are independently movable with respect to one another to desired, customizable positions close to the body of the patient. Calibration transducers determine the relative positions of the field transducers with respect to one another after they are located in their desired positions. Non-ionizing fields are transmitted and detected between the probe and reference field transducers. From the detected fields, the relative disposition of the probe with respect to the reference field transducers is determined.

31 Claims, 4 Drawing Sheets

U.S. PATENT DOCUMENTS

| | | | |
|---|---|---|---|
| 4,592,356 A | 6/1986 | Gutierrez | |
| 4,613,866 A | 9/1986 | Blood | 343/448 |
| 4,642,786 A | 2/1987 | Hansen | 364/559 |
| 4,651,436 A | 3/1987 | Gaal | 33/533 |
| 4,710,708 A | 12/1987 | Rorden et al. | 324/207 |
| 4,788,987 A | 12/1988 | Nickel | |
| 4,849,692 A | 7/1989 | Blood | 324/208 |
| 4,869,238 A | 9/1989 | Opie et al. | |
| 4,905,698 A | 3/1990 | Strohl, Jr. et al. | |
| 4,917,095 A | 4/1990 | Fry et al. | |
| 4,921,482 A | 5/1990 | Hammerslag et al. | 604/95 |
| 4,931,059 A | 6/1990 | Markham | 606/185 |
| 4,945,305 A | 7/1990 | Blood | 324/207.117 |
| 5,002,137 A | 3/1991 | Dickinson et al. | 175/19 |
| 5,042,486 A | 8/1991 | Pfeiler et al. | |
| 5,059,197 A | 10/1991 | Urie et al. | 604/164 |
| 5,078,144 A | 1/1992 | Sekino et al. | |
| 5,099,845 A | 3/1992 | Besz et al. | |
| 5,125,924 A | 6/1992 | Rudko | 606/12 |
| 5,125,926 A | 6/1992 | Rudko et al. | 606/19 |
| 5,158,084 A | 10/1992 | Ghiatas | |
| 5,172,056 A | 12/1992 | Voision | 324/207.17 |
| 5,195,540 A | 3/1993 | Shiber | 128/898 |
| 5,195,968 A | 3/1993 | Lundquist et al. | 604/95 |
| 5,197,482 A | 3/1993 | Rank et al. | |
| 5,211,165 A | 5/1993 | Dumoulin et al. | |
| 5,215,680 A | 6/1993 | D'Arrigo | 252/307 |
| 5,217,484 A | 6/1993 | Marks | 606/200 |
| 5,234,426 A | 8/1993 | Rank et al. | 606/1 |
| 5,251,635 A | 10/1993 | Dumoulin et al. | |
| 5,253,647 A | 10/1993 | Takahashi et al. | |
| 5,255,680 A | 10/1993 | Darrow et al. | |
| 5,265,610 A | 11/1993 | Darrow et al. | |
| 5,267,960 A | 12/1993 | Hayman et al. | 604/106 |
| 5,273,025 A | 12/1993 | Sakiyama et al. | |
| 5,275,166 A | 1/1994 | Vaitekunas et al. | |
| 5,295,484 A | 3/1994 | Marcus et al. | |
| 5,295,486 A | 3/1994 | Wollschager et al. | |
| 5,301,682 A | 4/1994 | Debbas | |
| 5,309,913 A | 5/1994 | Kormos et al. | |
| 5,325,873 A | 7/1994 | Hirschi et al. | 128/899 |
| 5,368,564 A | 11/1994 | Savage | 604/95 |
| 5,368,592 A | 11/1994 | Stern et al. | 606/33 |
| 5,373,849 A | 12/1994 | Maroney et al. | |
| 5,375,596 A | 12/1994 | Twiss et al. | |
| 5,377,678 A | 1/1995 | Dumoulin et al. | |
| 5,380,316 A | 1/1995 | Aita et al. | |
| 5,383,454 A | 1/1995 | Bucholz | |
| 5,383,874 A | 1/1995 | Jackson et al. | 606/1 |
| 5,383,923 A | 1/1995 | Webster, Jr. | 607/125 |
| 5,385,148 A | 1/1995 | Lesh et al. | |
| 5,389,096 A | 2/1995 | Aita et al. | 606/15 |
| 5,391,199 A | 2/1995 | Ben Haim | 607/122 |
| 5,403,356 A | 4/1995 | Hill et al. | 607/14 |
| 5,404,297 A | 4/1995 | Birk et al. | 362/421 |
| 5,409,004 A | 4/1995 | Sloan | |
| 5,423,321 A | 6/1995 | Fontenot | |
| 5,425,367 A | 6/1995 | Shapiro et al. | |
| 5,425,382 A | 6/1995 | Golden et al. | 128/899 |
| 5,429,132 A | 7/1995 | Guy et al. | |
| 5,431,168 A | 7/1995 | Webster, Jr. | |
| 5,433,198 A | 7/1995 | Desai | |
| 5,437,277 A | 8/1995 | Dumoulin et al. | |
| 5,443,489 A | 8/1995 | Ben-Haim | 607/115 |
| 5,450,846 A | 9/1995 | Goldreyer | |
| 5,465,717 A | 11/1995 | Imran et al. | |
| 5,471,982 A | 12/1995 | Edwards et al. | |
| 5,471,988 A | 12/1995 | Fujio et al. | |
| 5,480,422 A | 1/1996 | Ben-Haim | 607/122 |
| 5,483,951 A | 1/1996 | Frassica et al. | 600/104 |
| 5,487,391 A | 1/1996 | Panescu | |
| 5,538,008 A | 7/1996 | Crowe | |
| 5,554,152 A | 9/1996 | Aita et al. | 606/7 |
| 5,555,883 A | 9/1996 | Avitall | |
| 5,558,091 A | 9/1996 | Acker et al. | |
| 5,558,092 A | 9/1996 | Unger et al. | |
| 5,577,502 A | 11/1996 | Darrow et al. | |
| 5,588,432 A | 12/1996 | Crowley | |
| 5,617,857 A | 4/1997 | Chader et al. | |
| 5,622,169 A | 4/1997 | Golden et al. | |
| 5,715,822 A | 2/1998 | Watkins et al. | |
| 5,729,129 A | 3/1998 | Acker | 324/207.12 |

OTHER PUBLICATIONS

| | | |
|---|---|---|
| WO | WO 94/23647 | 10/1994 |
| WO | WO 94/28782 | 12/1994 |
| WO | WO 95/05773 | 3/1995 |
| WO | WO 95/07657 | 3/1995 |
| WO | WO 95/09562 | 4/1995 |
| WO | WO 95/10226 | 4/1995 |
| WO | WO 95/19738 | 7/1995 |
| WO | WO 96/05768 | 2/1996 |
| WO | WO 96/41119 | 12/1996 |
| WO | WO 97/03609 | 2/1997 |
| WO | WO 97/29678 | 8/1997 |
| WO | WO 97/29679 | 8/1997 |
| WO | WO 97/29683 | 8/1997 |
| WO | WO 97/29684 | 8/1997 |
| WO | WO 97/29685 | 8/1997 |
| WO | WO 97/29701 | 8/1997 |
| WO | WO 97/29709 | 8/1997 |
| WO | WO 97/29710 | 8/1997 |
| WO | WO 97/29803 | 8/1997 |
| WO | WO 97/32179 | 9/1997 |

INDEPENDENTLY POSITIONABLE TRANSDUCERS FOR LOCATION SYSTEM

This application claims the benefit of U.S. Provisional application Ser. No. 60/011,720, filed Feb. 15, 1996 and U.S. Provisional application Ser. No. 60/012,241, filed Feb. 26, 1996.

TECHNICAL FIELD

The present invention relates to systems for medical diagnosis and treatment, and specifically to using reference field transducers and medical probes with probe field transducers to detect the position, orientation, or both of the probe within the body of a patient.

BACKGROUND ART

There are many medical procedures in which probes, such as catheters, are introduced into the body of a subject or patient. In procedures such as cardiac catheterization and neurosurgery, it is often necessary for the physician or surgeon to know the location of the distal end of the probe inside the body. Although imaging methods such as fluoroscopy and ultrasound are sometimes used for this purpose, they are not always practical or desirable. For example, such systems typically require continuous imaging of the probe and patient during the procedure. In addition, fluoroscopic systems are often undesirable because that they expose the patient and physician to substantial ionizing radiation.

A number of locating systems for detecting the position of a probe or a catheter tip in the body of a patient without the need for continuous imaging of the patient have been proposed. These systems include, for example, those disclosed in U.S. Pat. Nos. 5,558,091; 5,391,199; 5,443,489; and International Patent Publications WO 94/04938 and WO 96/05768, the disclosures of which are hereby incorporated herein by reference. Other electromagnetic tracking systems, not necessarily for medical applications, are described in U.S. Pat. Nos. 3,644,825, 3,868,565, 4,017,858, 4,054,881 and 4,849,692.

Systems such as those disclosed in the '091, '199 and '489 patents and in the '938 PCT application determine the disposition (i.e., position, orientation, or both) of a probe using one or more field transducers, such as a Hall effect devices, magnetoresistive devices, coils or other antennas carried on the probe. The transducers are typically located at or adjacent the distal end of the probe or at a precisely known location relative to the distal end of the probe. Such systems further utilize one or more reference field transducers disposed outside the body to provide an external frame of reference. The reference field transducers are operative to transmit or detect non-ionizing fields or field components such as magnetic field, electromagnetic radiation or acoustical energy such as ultrasonic vibration. By transmitting fields between the external reference field transducers and the probe field transducers, characteristics of the field transmissions between these devices can be determined and then used to determine the position and orientation of the probe in the external frame of reference.

As described, for example, in the aforementioned '091 patent, the frame of reference of the external field transducers can be registered with the frame of reference of imaging data such as magnetic resonance imaging data, computerized axial tomography ("CAT") data, or conventional x-ray imaging data, and hence the position and/or orientation data derived from the system can be displayed as a representation of the probe superimposed on an image of the patient's body. The physician can use this information to guide the probe to the desired location within the patient's body, and to monitor its location and orientation during treatment or measurement of the internal body structure. This arrangement greatly enhances the ability of the physician to navigate the distal end of the probe through bodily structures and offers significant advantages over conventional methods of navigating probes within the body by feel alone. Because it does not require acquiring an optical image of the surrounding tissues for navigation purposes, it can be used with probes which are too small to accommodate optical elements. These transducer-based systems also avoid the difficulties associated with navigation of a probe by continuous imaging of the probe and patient during the procedure and avoids, for example, prolonged exposure to ionizing radiation inherent in fluoroscopic systems.

Such systems typically utilize reference field transducers or coils which are provided in a fixed, immovable array, in locations such as on the ceiling of an operating room or rigidly fixed to operating or catheterization table. In medical applications, where the system is used to track the location of a probe inside the body of a patient, the coil mounting may interfere with free access by the physician to the patient.

For example, the aforementioned '938 publication describes a catheter system which uses a plurality of non-concentric coils adjacent to the distal end of the catheter. These coils generate signals in response to externally applied magnetic fields, which allow for the computation of six location and orientation coordinates, so that the disposition of the catheter is known without the need for simultaneous imaging. Preferably, at least three such coils or radiators are arrayed in fixed locations outside the body, adjacent to the area of the body into which the catheter is introduced. For example, in cardiac catheterization, during which the patient is typically supine, three radiators are typically fixedly placed beneath the patient's thorax, in a fixed coplanar, triangular arrangement, with the centers of the coils from about 2 to 40 cm apart. For detection of the position and orientation of catheters or probes inserted into the brain, the transducers or field radiating coils should desirably be positioned adjacent to the patient's head. In neurosurgery, however, the patient is often in a seated, upright position or else face-down. Thus, a triangular frame holding the three radiators as described above cannot be comfortably and stably positioned below the head. However, positioning the frame above or beside the head will generally interfere with the surgeon's manipulation of probes and surgical tools.

It would therefore be desirable to enhance the accuracy and efficacy of probe tracking systems as described above, and other types of systems involving application of electromagnetic or other non-ionizing energy fields to a human body, by adjusting and optimizing the positions of the reference field transducers. Flexibility of placement of the transducers would allow custom positioning of the transducers to move them to the best possible locations to increase sensitivity of the locating system.

DISCLOSURE OF THE INVENTION

One aspect of the present invention provides a system for determining disposition of a probe within the body of a patient. A system in accordance with this aspect of the invention desirably includes a probe having one or more probe field transducers mounted thereon. One or more reference field transducers are also provided. As used in this disclosure, the term "field transducer" encompasses a device which can transmit a non-ionizing field such as a magnetic, electromagnetic, acoustic or optical field and also encompasses a device which can detect one or more components of such a field. In a system according to this aspect of the present invention, the reference field transducers are independently movable with respect to one another and are locatable by the user in desired, user-selected, customizable positions with respect to the body of the patient. Most preferably, the system includes means for mounting the reference field transducers on the body of the patient. In a particularly preferred arrangement, the reference field transducers are mechanically unattached to one another, so that each reference field transducer can be placed in any disposition desired by the user without mechanical constraints imposed by placement of the other reference field transducers. Calibration means are provided for determining the relative dispositions of the field transducers with respect to one another while the reference field transducers are located in the desired positions as, for example, while the reference field transducers are mounted on the patient's body. As used in this disclosure with reference to a single object, the term "disposition" refers to the position of the object, the orientation of the object, or both. As used in this disclosure with reference to any two objects, the term "relative disposition" refers to the direction from one object to the other, the distance from one object to the other, or both, and also includes the orientation of each object in the frame of reference of the other object. Most preferably, the calibration means is arranged to fully determine all parameters of the relative disposition of the field transducers with respect to one another, so that the distances and directions from each field transducer to each other field transducer, and the orientations of all of the field transducers, are fully known.

The system further includes transmission means to actuate the reference field transducers and probe field transducers so as to transmit one or more non-ionizing fields between the reference field transducers and the probe field transducer or transducers and detect each such transmitted field. For example, in a system where the transmission means actuate the reference field transducers to transmit a magnetic or electromagnetic field, the probe field transducer detects properties of the field received at the probe field transducer or transducers. Calculation means are also provided to determine the disposition of the probe in the frame of reference of the reference field transducers. This calculation proceeds from properties of the detected fields and from the relative dispositions of the reference field transducers with respect to one another.

Because the reference field transducers are independently positionable on or near the patient, they can be placed in an optimum arrangement to provide good sensitivity and signal to noise ratio in the particular area of interest, where a probe must be located during a particular procedure. Also, location of the reference field transducers can be selected to provide unimpeded access for surgical or other medical procedures. As further explained below, the frame of reference defined by the reference field transducers can be registered with the frame of reference of a previously acquired image, and a representation of the probe can be displayed superposed on the previously acquired image. In preferred embodiments where the reference field transducers are mounted on the patient's body, the frame of reference defined by the reference field transducers moves with the patient. Therefore, registration with a previously acquired image can be maintained without a need for the adjustment or reregistration despite movement of the patient. In systems according to further embodiments of the invention, the calibration means and calculation means are arranged to redetermine the relative dispositions of the reference field transducers periodically and to redetermine the disposition of the probe based upon the redetermined relative dispositions of the reference field transducers. For example, the system may operate cyclically, so that each cycle includes redetermination of the relative dispositions of the reference field transducers as well as determination of the probe disposition. Stated another way, the frame of reference of the reference field transducers is updated before each measurement of probe disposition. Alternatively, the reference field transducer disposition may be updated periodically. These systems permit mounting of the reference field transducers on movable elements of the body as, for example, on the surface of the abdomen or thorax.

The calibration means may include one or more calibration field transducers mounted to one or more of the reference field transducers. Thus, one or more of the reference field transducers is provided in a reference assembly with one or more calibration field transducers. The calibration means is arranged to determine the relative dispositions of the reference field transducers by detecting non-ionizing, fields transmitted to or from the calibration field transducers as, for example, field transmitted from the reference transducers of other reference assemblies.

Further aspects of the present invention provide methods of determining the disposition of a probe within the body of a patient. Methods according to this aspect of the invention desirably include the steps of providing a probe as aforesaid having one or more probe field transducers and positioning a plurality of reference field transducers positionable independently with respect to one another in desired, user-selected customizable positions with respect to the body of the patient. As discussed above in connection with the apparatus, the relative dispositions of the reference field transducers with respect to one another are determined while the reference field transducers are located in their desired positions. The probe is then located by transmitting one or more non-ionizing fields between the probe field transducers and reference field transducers and detecting these fields. The relative disposition of the probe with respect to the reference field transducers is determined from the properties of the detected fields and from the relative dispositions of the reference field transducers with respect to one another. As discussed above in connection with the apparatus, the relative dispositions of the reference field transducers desirably are redetermined frequently.

Still further aspects of the present invention include apparatus for generating or detecting non-Ionizing fields transmitted to or from within the body of a patient. Aspects according to this aspect of the invention includes a plurality of reference field transducers and means for positioning each of the reference field transducers independently with respect to one another in desired, customizable positions in close proximity to the body of a medical patient. Apparatus according to this aspect of the present invention can be utilized in the systems and methods discussed above. The positioning means may incorporate means for securing each reference field transducer to the body of the patient as, for example, adhesive means or other fastening devices which can engage the body. Yet another aspect of the present invention includes a kit incorporating a plurality of separate reference field transducers and means such as adhesives or other fastening devices for securing the reference field transducers to the body of the patient. A still further aspect of the present invention includes a reference field transducer assembly which incorporates a coil or other field transducer that generates heat during operation and a housing structure containing such coil. The assembly has a front surface which lies against the patient during operation and a rear surface. Means are provided in the housing for limiting heating of the front surface by heat generated in the coil. For example, the housing may include thermal insulation disposed between the coil and the front surface and preferably also includes means for dissipating heat within the housing or through the rear surface. These and other objects, features and advantages of the present invention will be more readily apparent from the detailed description set forth below taken in conjunction with the accompanying drawings.

MODES FOR CARRYING OUT THE INVENTION

A system in accordance with one embodiment of the invention is used in conjunction with an elongated probe in the form of a tube or catheter 20 having a proximal end 22 and a distal end 24. A probe body 28 incorporating a probe field transducer or position sensor 30 is physically connected to the distal end 24 of catheter 20. Probe field transducer 30 is preferably provided in the form of a sensor arranged to detect magnetic or electromagnetic fields. For example, the probe field transducer 30 may be a multi-axis, solid-state position sensor of the type disclosed in the aforementioned U.S. Pat. No. 5,558,091. Such a sensor incorporates a plurality of transducers sensitive to magnetic field components in mutually orthogonal directions. Other suitable position sensors include coils as disclosed in the aforementioned U.S. Pat. No. 5,391,199 and in International Publication WO 96/05768. Such coils may be provided as a single coil or as a plurality of orthogonal coils capable of detecting field components in orthogonal directions.

Elongated probe or tube 20 is constructed and arranged to be navigable within the body of the patient to a desired location. For example, tube 20 may have the structure of a conventional catheter, endoscope, laparoscope or the like. The size and shape of tube 20 will also depend upon the region of the body to be treated. The probe may incorporate essentially any device which can be inserted or advanced into the body to perform a medical procedure, such as for treatment, measurement or observation, and capturing tissue samples or other materials within the body. Tube 20 may also be constructed to accommodate a conventional intra-body medical instrument such as scissors or forceps, or other surgical tools operable from the proximal end or handle of the device. Such a surgical tool may be any conventional surgical tool of the type commonly used in endoscopic, arthroscopic or laparoscopic surgical procedures, or a conventional biopsy sampling device. However, it should be appreciated that essentially any instrument or device which can be inserted into the body may function as a probe, and hence the term "probe" should not be taken as limited to any specific configuration.

Figures 2, 3:
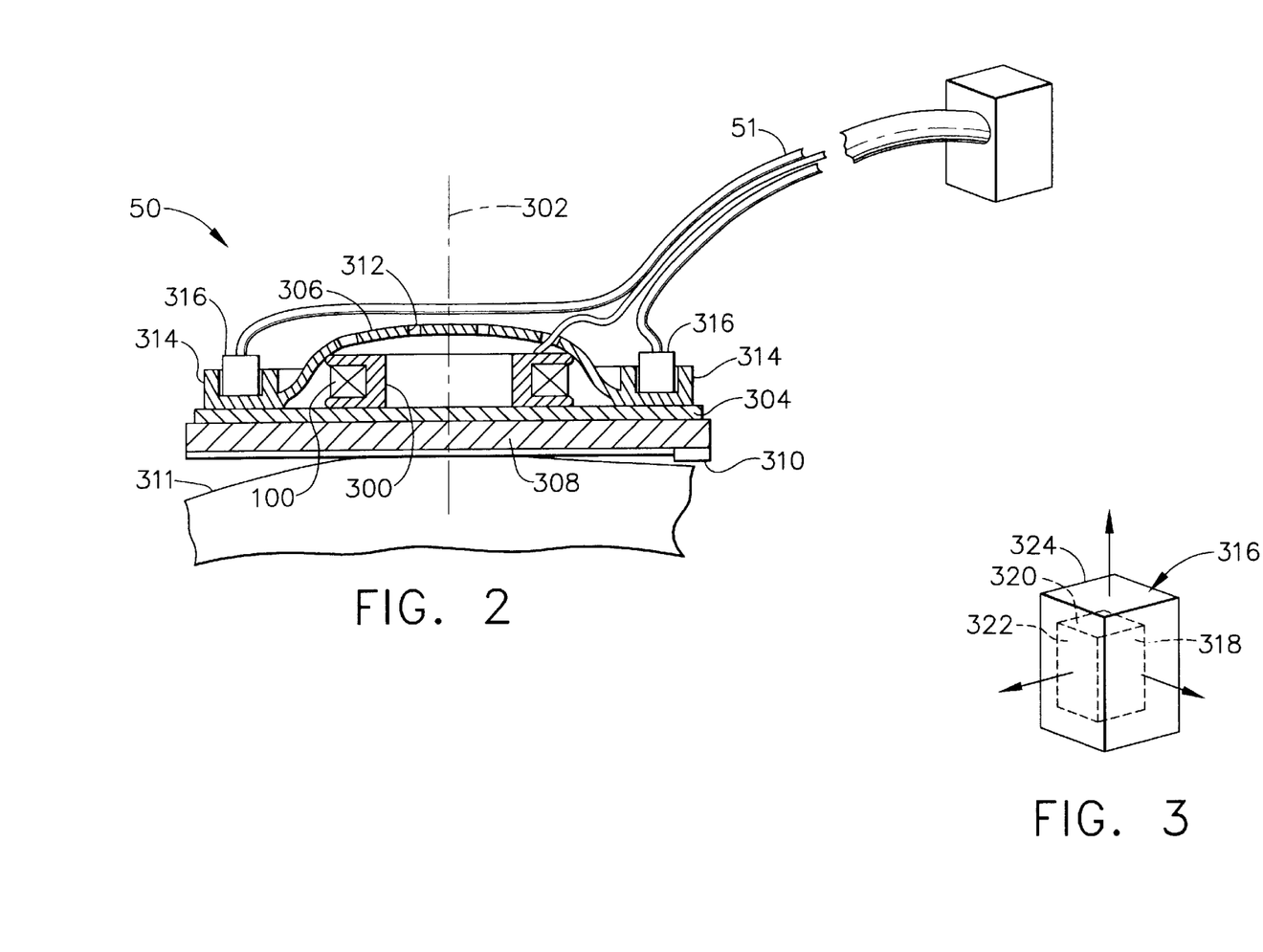
FIG. 2 is a diagrammatic sectional view depicting a transducer assembly in accordance with one embodiment of the invention.
FIG. 3 is a diagrammatic perspective view depicting one element of the assembly utilized in FIG. 1.
Figure 4:
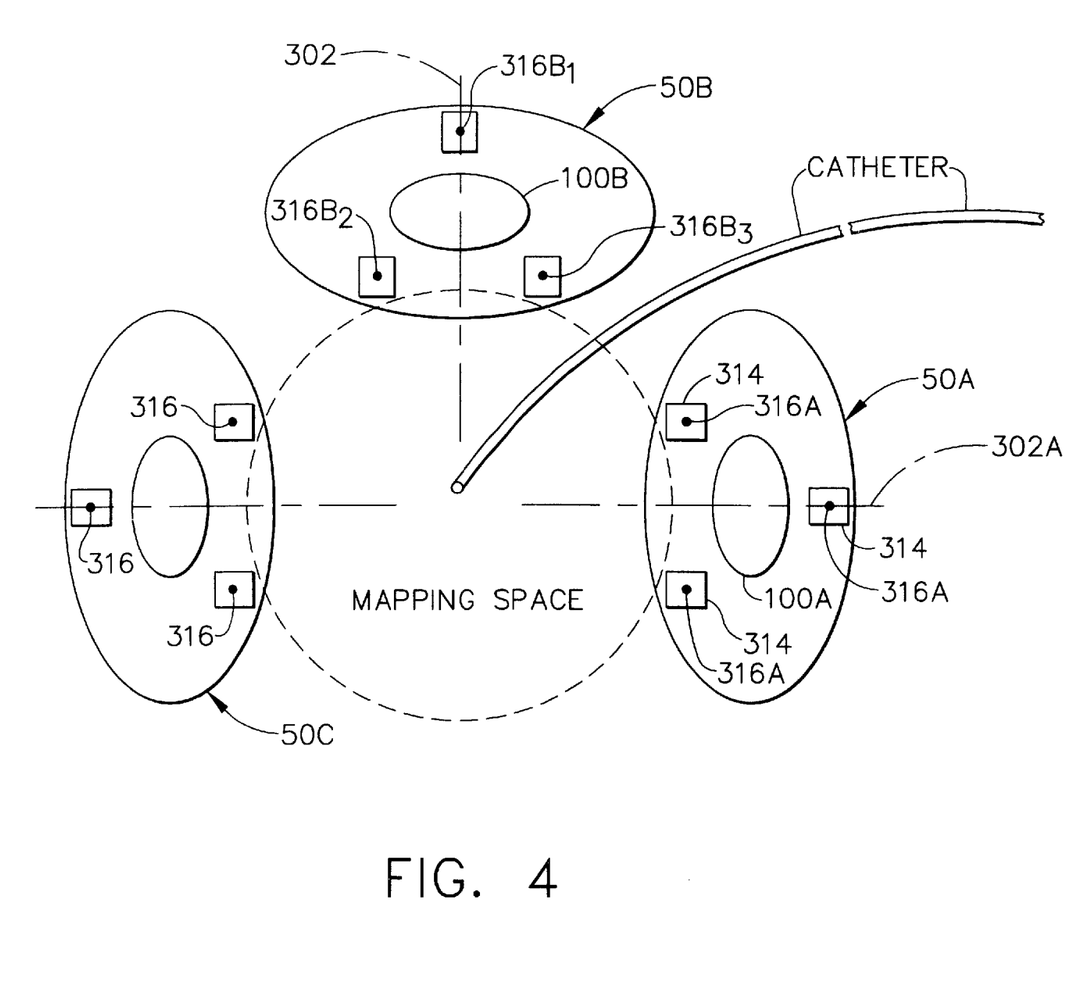
FIG. 4 is a diagrammatic view of components shown in FIGS. 1–3.

The apparatus further includes a set of reference assemblies 50, in this case three separate reference assemblies, which are mounted directly on the patient in desired, customizable positions. As best seen in FIGS. 2 and 4, each reference transducer assembly 50 includes a cylindrical coil 100 fabricated from fine gauge wire. Such a coil preferably includes approximately 2000 turns of wire to form a coil with a diameter of 3 or 4 inches or less, and a height of ¼ inch or less. Coils such as these are currently sold as heater coils by Minco of Minneapolis, Minn. Each cylindrical coil is formed on a cylindrical bobbin 300 and defines a coil axis 302 concentric with the coil. Each reference assembly 50 further includes a housing incorporating a front panel 304 and a rear panel 306. These elements may be formed from non-ferromagnetic materials such as polymers, non-ferromagnetic metals and other materials conventionally used in disposable medical devices. Front panel 304 is provided with a cushioning layer 308 which in turn has an adhesive coating on its exposed front surface 310. Front panel 304 and hence its exposed, adhesive coated front surface 310 extend generally transverse to the coil axis 302. A layer of a peelable release film 311 may be removably positioned over surface 310. Layer 311 protects the adhesive on surface 310 during shipment and handling, but is removed during use of the assembly. In place of adhesive layer 310, the reference assembly can be provided with features such as elastic bands, straps, clamps or other devices for securing it to the body of a patient. Alternatively or additionally, the housing elements 304 and 306 can be provided with features such as holes or tie points for cooperation with user-supplied fastening devices such as sutures for holding the assembly in place. In a further variant, the fastening features can be provided directly on the reference field transducer or coil 100, as on bobbin 300, and the housing elements can be omitted.

Rear surface 306 is provided with vents 312 to permit dissipation of heat generated during operation of coil 100. Other known features for promoting conduction and dissipation of heat can be provided in the rear panel. For example, the rear panel can be equipped with fins, and can be fabricated from a highly heat conductive non-magnetic material such as aluminum. Alternatively or additionally, the region within the housing surrounding coil 100 can be filled with a material having a high specific heat or with a fusable material adapted to melt and take up heat in latent heat of fusion, preferably at a temperature slightly above normal body temperature such as about 40–50° C. Other known devices for cooling an electrical assembly can be provided as, for example, coils for circulating a cooling medium such as water or air within the assembly or to an external heat transfer device can be provided. Thermoelectric cooling devices may also be used. These heat dissipating and heat absorbing features are intended to limit the temperature rise of the front surface 310 of the front panel. As further discussed below, the front panel will lie against the patient during operation. Front panel 304 and cushioning layer 308 may have substantial heat-insulating properties, which also help to limit the temperature rise of front surface 310.

A plurality of calibration transducer sockets 314 are formed integrally with the housing at fixed positions relative to coil 100. As best seen in FIG. 4, each transducer assembly 50 has three sockets 314 disposed around the periphery of coil 100. In the particular configuration illustrated, the sockets are disposed desirably at spaced locations around the coil axis 302 and thus form vertices of a triangle in a plane perpendicular to coil axis 302. Each socket 304 is adapted to receive a calibration field transducer 316 and to hold the calibration field transducer in a predetermined position and orientation relative to the coil 100 of the same reference assembly 50. As best seen in FIG. 3, each calibration field transducer 316 desirably includes a set of three orthogonal transducer elements 318, 320 and 322 adapted to detect magnetic field components in three mutually orthogonal directions. The active transducer elements may be solid state transducers such as Hall-effect or magnetoresistive transducers. Alternatively, the active elements may be coils wound on mutually intersecting axes. The active elements 318, 320 and 322 are housed in an outer package or housing 324. Each socket 314 and/or the housings 324 of the calibration field transducers 316 and the sockets 314 may include conventional features such as snaps, pins, clasps and other features for mechanical fastening. Alternatively or additionally, the housing 324 of the calibration transducers may be adapted to fit closely within sockets 314, so that each housing is held in an accurate, repeatable position with respect to coil 100. In yet another alternative, the housings 324 of the calibration transducers 316 can be formed integrally with the coil housing elements 304 and 306, may be formed integrally with the coil bobbin 300 or may be otherwise attached permanently to the coil bobbin or housing.

The reference field transducers or coils 100, and the calibration field transducers 316 of the various reference assemblies 30 are connected through leads 51 to a field transmitting and receiving device 80. Preferably, reference assemblies 50 are removably detachable from leads 51 to allow easy replacement and/or disposal after use. Providing disposable reference assemblies is advantageous since resterilization of the transducers, which may cause damage to the sensitive transducers, can be eliminated. In addition, providing detachable transducers allows further customization by allowing interchangeability among different sized reference assemblies for different medical procedures and patient sizes. As an alternative to leads 51, the various transducers on each reference assembly can be connected to the transmitting and receiving device 80 through wireless telemetry, as by RF or infrared telemetry. In this case, each reference assembly 50 may include a self-contained power supply such as a battery.

Figure 1:
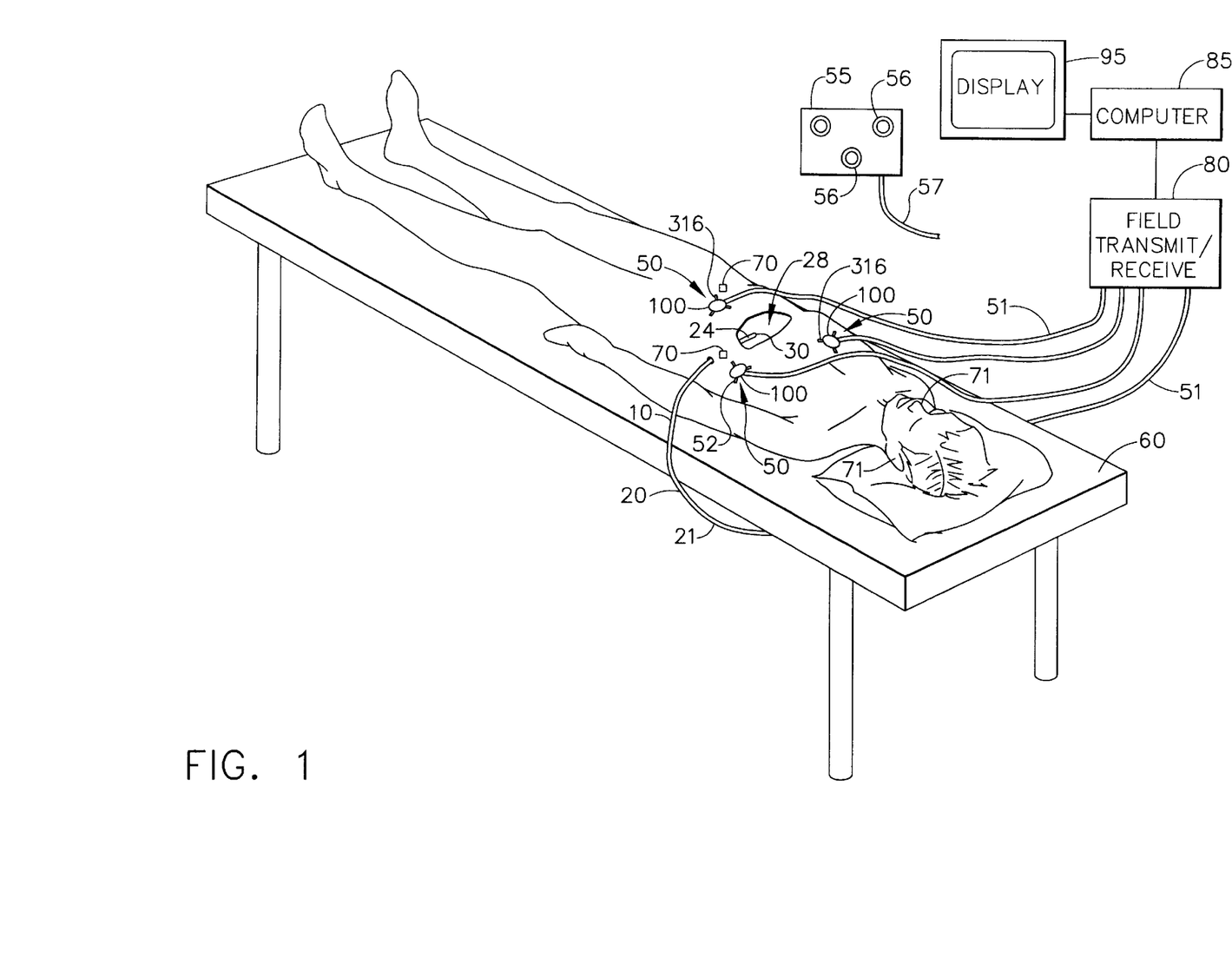
FIG. 1 is a perspective view of a preferred embodiment of the present invention showing reference field transducers attached to the body of the patient.

Field transmitting and receiving device 80 is connected to a computer 85, which can consist of a microcomputer, work station, mainframe or other similar computing device, which in turn is connected to a display device, such as cathode ray tube (CRT) monitor 95. Field transmitting and receiving device 80 and computer 85 are arranged to cooperate with the probe field transducers 30 and coils reference field transducers 100 to transmit and receive non-ionizing fields, preferably electromagnetic fields, to determine the disposition of the probe 28 in the frame of reference of the reference field transducers 100. As best seen in FIGS. 1 and 4, reference assemblies 50 are mounted to the patient at arbitrary, user selected dispositions by adhering the front surfaces 310 to the patient. That is, the dispositions of the reference assemblies 50, and hence the dispositions of the reference field transducers 100 can be selected as desired by the physician or other person mounting the reference assemblies. Preferably, the reference assemblies are mounted so as to place the various coils or reference transducers 100 in proximity to a region of interest within the patient, i.e., in proximity to a region where the distal tip of probe 28 is to be employed. The particular dispositions illustrated in FIGS. 1 and 4 are intended merely for purposes of illustration and should not be taken as limiting the positions in which the reference field transducers can be placed. For example, the reference assemblies can be placed in a generally coplanar arrangement on the patient's back, with the coil axes 302 extending generally parallel to one another so that the coil axes surround the center of the region of interest. Alternatively, the various field transducers can be placed in a generally U-shaped arrangement, as depicted in FIG. 4, so that the axes 302 of the reference transducers or coils 100 in all of the reference assemblies converge in the region of interest.

When positioned on the patient, the reference field transducers 100 define an external frame of reference. Electromagnetic or magnetic fields can be transmitted between reference field transducers 100 and the transducer 30 on the probe, such that the disposition of the probe field transducer and probe 28 can be calculated from the characteristics of the fields, such as strength and direction, as detected by the probe field transducer. Thus, the reference field transducers 100 and the probe field transducer 30 cooperatively define a plurality of transmitter-receiver pairs. Each such pair includes one transmitter and one receiver as elements of the pair. One element of each such pair is disposed on the probe and the other element of each such pair is disposed in the frame of reference defined by the reference field transducers 100. Typically, at least one element of each transmitter-receiver pair is disposed at a different position or orientation than the corresponding element of the other pairs. By detecting the characteristics of field transmissions between the elements of the various pairs, the system can deduce information relating to the disposition of the probe in the external frame of reference defined by the reference field transducers. The disposition information can include the position of the probe, the orientation of the probe, or both. However, the calculation relies upon the reference field transducers being positioned in known positions and orientations relative to one another.

In the system of FIGS. 1–4, because the reference field transducers 100 may be placed at any desired location and orientation relative to one another, it is necessary to calculate their locations with respect to one another. Calibration field transducers 316 cooperate with reference field transducers or coils 100 to provide the information necessary to calculate the position and orientation of the reference assemblies relative to one another. The coil 100 of each reference assembly 50 constitutes a single axis field transducer, whereas the calibration field transducers 316 of each reference assembly 50 represent a system of three three-axis transducers disposed at known locations with respect to one another. For example, the three calibration transducers 316B, 316B2, and 316B3 of reference assembly SOB are at known locations relative to one another. As described, for example, in International Patent Publication WO 94/04938, the disclosure of which is incorporated by reference herein, the position and orientation of a single axis field transducer such as coil 100A can be fully deduced by actuating coil 100A to produce a magnetic field and detecting the magnetic field components in each of three mutually orthogonal directions at each of the three calibration transducers 316B1, 316B2 and 316B3. The algorithm utilized in the aforementioned 94/04938 Publication is used therein for an entirely different purpose, namely, location of a probe relative to multiple reference transducers which are already in known position relative to one another. Nonetheless, such algorithm can be applied directly to the problem of finding the position and orientation of coil 100A with respect to the calibration sensors on reference assembly 50B. In an initial stage, the algorithm proceeds by treating the reference field transducer coil 100A as if it were a uniform radiator, and ignoring the effect of orientation of coil 100A on the field component magnitudes determined at calibration transducers 316B. Stated another way, in this initial stage coil 100A is treated as if it radiated a spherical field. Using this assumption, and the field component magnitudes detected calibration transducers 316B, the system arrives at an initial estimate of the position of coil 100A relative to reference assembly 50B. Using that initial estimate of position and the detected field component magnitudes at calibration transducers 316B, the system then calculates orientation angles for coil 100A. Using the newly-calculated orientation angles, the system calculates a better estimate of position. The last two steps are repeated until new estimate of position matches the last previous estimate of position within a preselected tolerance. Stated another way, the system converges to the correct position and orientation angles. Further details of the algorithm are given in the '938 Publication. The same algorithm can be used to find the location of coil 100C with respect to reference assembly 50C. Likewise, by actuating coil 100B on reference assembly 50B, the position and orientation of coil 100B with respect to assembly 50C can be determined by monitoring signals from the three, three-axis calibration field transducers 316 on reference assembly 50C. The location of coil 100B with respect to reference assembly 50A can be determined from the signals generated by calibration field transducers 316A on reference assembly 50A while coil 100B is active. Similarly, when coil 100C is activated, the disposition of coil 100C with respect to assemblies 50A and 50B can be determined. The system provides redundant information, including two independently determined sets of position and orientation parameters defining the relative dispositions of each pair of reference assemblies. This redundant information can be used in checking the values obtained and in arriving at an estimate for the true values which minimizes the total error in the system. For example, by comparing the two independently-determined values of relative disposition of pair of assemblies, an estimate of the error for that pair can be obtained. Similar estimates can be obtained for the error in relative dispositions of other pairs of reference assemblies. Using an iterative process, the computer can select estimates of the true dispositions of the various reference assemblies which yield the lowest total error. Alternatively, the two estimates of relative disposition for each pair of reference assemblies can simply be averaged with one another.

In a further alternative arrangement, the system can be modified to use fewer calibration transducers and thereby eliminate some of the redundant information. Thus, for the system as shown in FIGS. 1–4 in which three reference field transducers 100 are shown, there need not be three calibration field transducers 316 on each reference assembly in order to calibrate or determine the relative positions of the reference field transducers with respect to one another after they are placed. Namely, there need only be enough transmitter-receiver pairs as between the reference and calibration field transducers to determine the locations of the reference assemblies with respect to one another. For instance, in the system of FIGS. 1–4, where the reference field transducers comprise single-axis field transmission coils, a system using only three, three-dimensional field receiving calibration transducers on only one reference assembly will allow determination of the relative positions and orientations of the three transmitting coils with respect to one another. Alternatively or additionally, the reference field transducers can function as calibration transducers. For example, if coil 100A is energized with an alternating current, the alternating field can be detected by reference field transducers 100B and 100C of the other reference assemblies. Those signals provide additional information which can be used in the calibration process.

In another preferred embodiment, a fixed array of calibration field transducers is provided, such as calibration array 55 (FIG. 1) which includes a plurality of calibration field transducers 56 attached to field transmitting and receiving device 80 through leads 57. Because the transducers 56 of the calibration array are provided in fixed, known relationship with respect to one another, the individual positions of each of the reference field transducers with respect to the array transducers can be determined in accordance with the algorithms disclosed, for example, in the aforementioned '938 International Publication. Once the positions of reference field transducers 100 in the frame of reference of calibration array 55 have been determined, the dispositions of the reference field transducers relative to one another can be calculated directly. In this arrangement, the calibration field transducers can be omitted from the reference assemblies 50.

Once the calibration of the reference field transducers is completed, the disposition of the probe in the external reference frame defined by the reference field transducers can be determined as set forth for instance in the '091 patent, by transmitting and receiving non-ionizing fields between the reference field transducers and the probe field transducers.

In a method according to one embodiment of the invention, the patient is positioned on the patient bed 60 and the reference assemblies 50 are independently positioned in desired arrangements on or near the patient. Next, the external frame of reference is determined by use of the calibration and reference field transducer pairs. Namely, the field transmitting and receiving unit 80 and computer 85 actuate the reference field transducers or the calibration field transducers to transmit and receive fields as discussed above. Using the above described method, the computer 85 calculates the disposition of the reference field transducers 100 with respect to one another to determine the external reference frame.

Next, the distal end of the probe 28 is advanced into the patient towards the area of interest, carrying the probe field transducer 30. The field transmitting and receiving unit 80 and computer 85 then actuate the external field transducers 100 and probe field transducer 30 to transmit and receive fields. For example, where the reference field transducers 100 are field transmitters, the probe field transducers will send signals representing the fields detected at the probe to the field transmit and receive unit. Conversely, where the probe field transducers are used as transmitters, drive signals are sent to the probe field transducers. The computer 85 then deduces the disposition of the probe field transducer 30 and thus deduces the disposition of the probe itself in the external frame of reference defined by the reference field transducers 100. As the dispositions of the reference field transducers 100 relative to one another are now known, the step of finding the disposition of the probe field transducer 30 can be performed by known techniques such as those taught in the '091 Patent and in the '938 Publication.

In some procedures, it is desirable to display the position of the probe on display 95 superposed on previously-acquired images of the patient such as MRI, CT or x-ray images. To do this, it is necessary to define a patient reference frame and then translate the position of the probe in the external frame of reference defined by transducers 100 to the patient frame of reference. Stated another way, the frame of reference of the reference assemblies 50 and reference field transducers 100 must be registered with the frame of reference of the image. This can be accomplished in several ways. In one technique, probe 28 and hence field transducer 30 are brought to several prominent points on the patient which are readily identifiable in the image as, for example, readily identifiable bone structures depicted in the image data. To facilitate this process, fiducial markers 71 can be fastened in place on the patient's body before the image is acquired, so that the fiducial markers are depicted in the image and are accessible to the probe. The data defining each prominent point or marker is supplied to the computer, as by positioning a cursor over the depiction of the point on display screen 95. When the physician brings probe 28 into engagement with each prominent points or fiducial markers, he supplies a manual input to the computer, whereupon the computer records the current position of probe 28 in the reference frame of the field transducers 100 as the position of the prominent point or marker in that reference frame. Data defining the position of each such point or marker in the image frame of reference is combined with data of defining the same points in the frame of reference of field transducers 100 to arrive at a transposition vector relating the two frames of reference to one another. Alternatively, the contour of a rigid element in the patient's body as, for example, the patient's face can be traced with the probe tip and matched to the same contour in the image frame of reference. In another approach, one or more registration marker field transducers 70 may be provided on fiducial markers which are attached to the patient prior to imaging. The system tracks disposition of the registration field transducers in the frame of reference of field transducers 100 in the same manner as it tracks disposition of the probe transducer 30, so that positions of the fiducial markers in the field transducer reference frame are known.

One major advantage provided by embodiments of the present invention where the reference field transducers are mounted directly to the patient is that the transducers define a reference frame that is fixed with respect to with the patient. In many cases, such as where the reference field transducers are mounted to rigid portions of the patient's body (such as on the head), the requirement that the patient be rigidly fixed in a given position to the patient bed is eliminated. This is because it is no longer necessary to prevent relative movement between the patient and the frame of reference defined by the reference field transducers typically mounted to the patient bed or attached to a wall or the ceiling. For instance if the reference field transducers are mounted to the head, movement of the head of the patient will not cause relative movement of the head with respect to the reference field transducers since they are positioned on the head, Stated another way, the frame of reference defined by reference assemblies 50 and reference field transducers 100 is fixed to the patient and moves alone with the patient. There is no need to recalibrate or reregister this frame of reference with respect to any fixed frame of reference.

Where the reference transducers are not fixed relative to one another as where the reference transducers are mounted on flexible or movable portions of the patient's anatomy, the system must recalibrate the position of the reference assemblies relative to one another. Such recalibration is performed by repeating the calibration steps discussed above including operation of the calibration field transducers and calculation of the relative dispositions of the reference assemblies. The recalibration can be performed periodically as, for example, every few seconds during operation. More preferably, recalibration is performed every time disposition of the probe 28 is determined. Thus, the system can operate cyclically. Each cycle includes a calibration stage, in which the relative dispositions of the reference assemblies and field transducers are established, and a measurement stage, in which the position and/or orientation of probe 28 is determined in the frame of reference of the reference assemblies and field transducers 100. The cycle may also include recalibration of registration information as, for example, location of one or more fiducial markers registration transducers 70. Even where the reference assemblies are mounted on a rigid portion of the body, periodic recalibration is desirable as an assurance against inadvertent movement of the reference assemblies.

In the embodiments described above, the various transducers are time-multiplexed. For example, the various reference field transducers are actuated at different times during each calibration cycle. Other multiplexing schemes, such as frequency-division and code division multiplexing schemes, can be used as well. Also, in the arrangements discussed above, all of the reference field transducers are arranged to transmit magnetic fields, whereas the calibration field transducers and probe field transducer are arranged to detect such fields. The reverse arrangement, where the probe and calibration field transducers are transmitters and the reference field transducers are detectors, can also be employed. In still other possible arrangements, the calibration field transducers include some transmitters and some detectors, so that relative positions of the various reference assemblies 50 can be determined by transmitting fields between calibration transmitters on different transducer assemblies. A mixed-mode arrangement, in which the reference and probe transducers employ one type of field, and the calibration transducers employ another type of field, can also be used. For example, in a system using magnetic or electromagnetic reference transducers, the calibration field transducers may be acoustic or optical transducers. Also, the various field transducers can have more or fewer axes of sensitivity than those discussed above. For example, the reference field transducers may be multi-axis field transducers, whereas the probe field transducer may be a single-axis field transducer. Particularly where the reference field transducers are multi-axis field transducers such as multiaxis coils, the reference field transducers can also serve as calibration transducers. That is, the relative dispositions of the reference assemblies can be deduced solely by detecting signals transmitted between the reference field transducers on different assemblies.

In yet another arrangement, the probe field transducer, or another movable field transducer, is used in place of the calibration transducers. During the calibration step, the movable field transducer is inserted successively in the various calibration probe sockets 314 of each field assembly while each reference coil is actuated. For example, the probe tip 28 may be moved from socket to socket. Provided that the probe sockets position the movable transducer at known locations on each reference assembly, and provided that the reference assemblies do not move relative to one another during the calibration step, this procedure yields the same information as simultaneous acquisition of multiple calibration probe signals in the embodiments described above.

Figure 5:
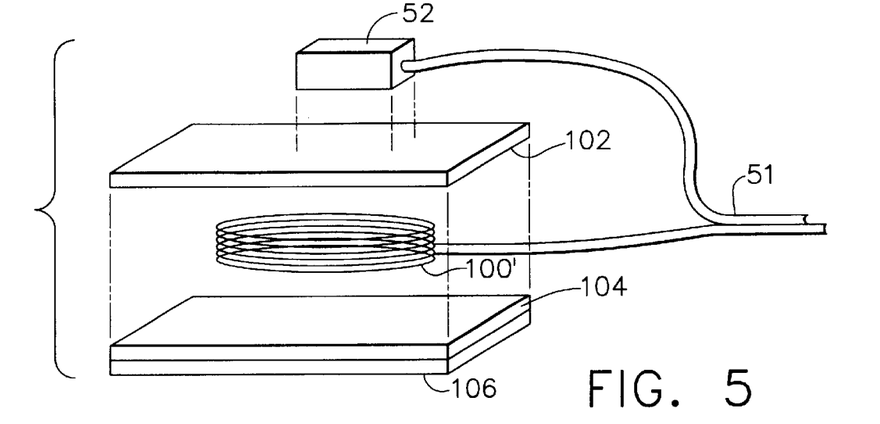
FIG. 5 is an exploded, perspective view of a reference field transducer and calibrating transducer assembly in accordance with one embodiment of the invention.

As shown in FIG. 5, a reference transducer assembly may include a coil or reference transducer 100' mounted between an upper or rear flexible layer 102 and a lower or front flexible layer 104. Double-sided adhesive tape 106 may be affixed to the bottom surface of lower layer 104 so that the entire coil assembly can be readily attached to the patient. One or more reference transducers 52 can be mounted on such an assembly, as on the upper layer 102.

Figure 6:
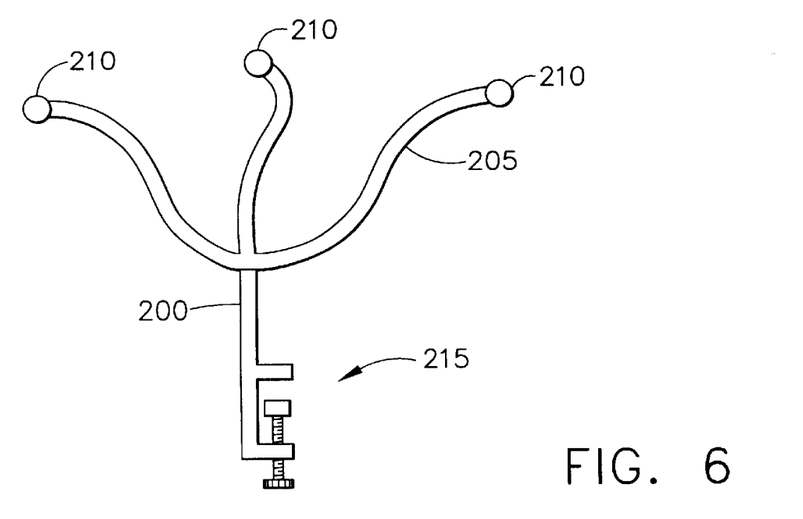
FIG. 6 is side perspective view of another preferred embodiment of the present invention in which the reference field transducers are independently movable.

In the embodiments discussed above, the reference transducers are mounted on the patient. However, the independently-positionable reference transducers also can be mounted at other locations near the patient. Turning now to FIG. 6, a further embodiment of the present invention is provided where the reference field transducers are attached to common structure yet are still independently movable with respect to one another. Here, a common support arm 200 is provided to which is attached a number of flexible, goose neck arms 205 to which reference field transducers 210 are attached. An adjustable mounting mechanism 215 is provided for attachment of the coil carrying structure to the patient bed or other desirable location. The relative positions of the field transducers with respect to one another may be determined after they are positioned as described above. It should be appreciated that there are a number of other effective ways to attach the reference field transducers to a common support structure to allow independent movement of the transducers, such as by using bendable wire arms, arms with adjustable linkage mechanisms or other such adjustable frames.

Figure 7:
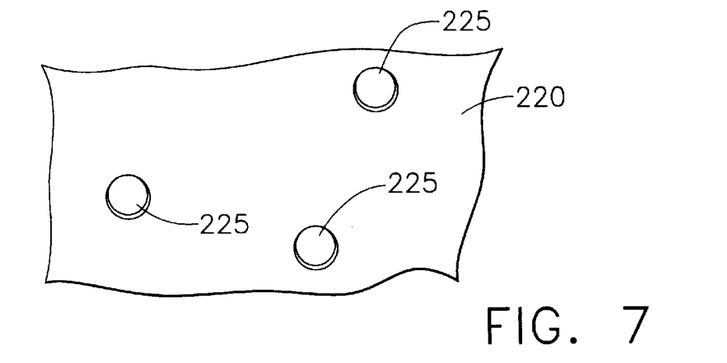
FIG. 7 is a front view of another preferred embodiment of the present invention in which the reference field transducers are independently movable on a flexible, sheet-like support.

A yet further embodiment of the present invention is shown in FIG. 7, in which a single sheet-like support 220 is provided to which reference field transducers 225 are attached. In this embodiment, the sheet can be positioned over or under the patient and each of the transducers can be moved to a desired location by gathering excess material of the sheet. Alternatively, the flexible sheet can be formed of a stiff, yet sufficiently flexible material so as to allow the sheet to be bent into any desired positions to allow adjustment of the positions of the field transducers.

The coil or transducer arrangements of the present invention solve a number of problems associated with fixed, non-movable coil systems. For instance, non-movable coil systems can interfere with the access of the surgeon. Non-movable coil systems generally cannot be positioned above the patient as they would block the lighting, and may not be positionable under the patient where a metal be would cause interference and not all beds can be replaced or retrofitted to eliminate this problem. Moreover, with non-movable coils, high accuracy mapping volumes are too small to be useful if the coils cannot be moved from moment to moment.

The present invention solves these problems since the reference field transducers can be positioned in a least obtrusive manner and can even be moved out of the way or to a new locale during the procedure. Moreover, the transducers can be moved closer to area of interest to provide better concentration of fields and better readings. The present invention further allows the use of even smaller reference transducers since there is no longer a need to provide large coils to generate fields over a large area to ensure broad coverage. In preferred embodiments, the transducers can be disposable allowing easy replacement of damaged or contaminated transducers and the use of different size and types of transducers for different applications. A kit of such reference field transducers, with or without the calibration field transducers, can also be provided for the physician and may contain identical transducers or transducers of different sizes for different applications.

The present invention can also be used in conjunction with the system disclosed in U.S. application Ser. No. 08/476,380, the disclosure of which is hereby incorporated by reference. In the '380 application, feedback is used to adjust the currents supplied to the reference field transducers or coils to ensure that the sensor on the probe receive fields within a preselected range of magnitudes regardless of the location of the probe. This ensures that the sensor operates within its optimal range and allows the use of compact transmitters and sensors. Thus, the feedback techniques disclosed in the '380 application can be used with the present invention to adjust the strengths of the non-ionizing fields generated by the reference field transducers and/or the probe field transducer.

The present invention may further be used in conjunction with the multiple probe system disclosed in the PCT application filed on even date herewith entitled "Medical Procedures And Apparatus Using Intrabody Probes" which claims the benefit of United States Provisional Applications No. 60/012,275, filed Feb. 26, 1996; 60/011,721, filed Feb. 15, 1996; and 60/031,824, filed Nov. 26, 1996 and which is commonly assigned to the assignee of the present application. The disclosures of said provisional applications are also incorporated by reference herein. In preferred embodiments of this system, a medical probe such as a catheter is guided within the body of a patient by determining the relative dispositions of the probe relative to another probe, as by transmitting non-ionizing radiation to or from field transducers mounted on both probes. In particular, a site probe may be secured to a lesion within the body, and an instrument probe for treating the lesion may be guided to the lesion by monitoring relative positions of the probes. In many embodiments of this system, it is not necessary to register the positions of the probes with image data, or to superpose probe locations on images. The independently movable reference field transducer arrangements of the present invention can therefore be used with the site probe/instrument probe system, with or without simultaneous patient imaging, to locate the dispositions of the probes in the frame of reference defined by the reference field transducers. So long as the dispositions of both probes are found in the same frame of reference, the relative disposition of the two probes can be determined. For example, the relative dispositions can be determined properly even if the reference field transducers move relative to one another (as where the field transducers are mounted on soft tissue), provided that the system is recalibrated to update the dispositions of the field transducers relative to one another during each cycle or whenever movement occurs. In a further variant, where the reference field transducers are mounted on parts of the body subject to repetitive natural movement, such as on the chest or other area which moves repetitively in the respiratory cycle, the system can be calibrated at a particular point in the natural movement cycle (e.g., end inspiration or end expiration) and can be actuated to determine the location of a probe at the same point in the natural movement cycle. Such a system can also be used where superposition of the probe representation on a previously-acquired image is desired as, for example, where the image is an image acquired at the same point of the natural movement cycle.

Superior signal-to-noise ratio performance is also achieved with the independently positionable reference field transducers of the present invention. In general, with the use one or more reference field transducers in a probe locating system, there is a region of volume associated with the field transducers in which the signal-to-noise ratio of the assembly is optimized (a so-called "optimal region"), where high-accuracy field measurements can be made by a probe transducer. With prior probe location systems in which the reference transducers are mounted in fixed positions about the patient bed, however, this optimal region will typically encompass a large area to account for all possible areas of interest. For example, a system using bed-mounted transducers may be required to locate the probe in the thorax of one patient and in the head of another patient. The larger the optimal regions, however, the more difficult it is to achieve a high signal-to-noise ratio throughout such region. With the independently positionable transducer assemblies of the present invention, this optimal area can be made smaller and highly concentrated. For each procedure, the optimal area can be configured to match the region where the probe is to be tracked. Accordingly, preferred embodiments of the present invention can provide enhanced signal-to-noise performance in comparison to a fixed transducer assembly using the same transducers in a large fixed array. The signal-to-noise performance of the system also depends on the properties of the probe transducer. The enhanced performance provided by preferred embodiments of the present invention can provide acceptable signal-to-noise performance with a less sensitive probe transducer, which in turn facilitates miniaturization of the probe transducer and probe.

Alternatively, the benefit provided by the movable transducer assembly can permit use of smaller, cheaper and less obtrusive reference transducers while maintaining satisfactory performance. Moreover, the reference field transducers can be positioned to provide optimum performance in that region without obstructing the physician's access to the patient. Merely be way of example, where the surgeon will operate through a craniotomy on the left side of the head, the reference assemblies can be placed on the back top and right side of the head.

Yet another advantage of the embodiments disclosed herein is the ability to provide adjustment of the reference field transducers if they are moved or if the initial positioning of the reference field transducers yields poor readings. Thus, the surgeon can relocate the reference assemblies, or even add additional reference assemblies, during a procedure.

It will be further appreciated that although aspects of the above preferred embodiments have been described with reference to a system for position determination based on magnetic fields, the present invention is equally applicable to other types of position determination systems known in the art, such as systems that use other forms of field transducers, such as those which radiate and detect electromagnetic, magnetic, acoustic, optical ultrasonic or other non-ionizing fields.

The method of using calibration field transducers for calibrating the relative positions of the reference transducers with respect to one another in accordance with the present invention can also be used to replace or augment the manner of determining the relative positions of the linked reference field transducers disclosed in the application entitled "Movable Transmit Or Receive Coils For Location System" filed on even date herewith and assigned to the assignee of the present application. Namely, instead of including a rotation measuring device, such as an optical encoder device, which allows the angle between transducer-carrying arms to be accurately determined so that the relative positions of reference field transducers are known, calibration field transducers can be used as disclosed herein.

As these and other variations and combinations of the features described above can be utilized without departing from the present invention, the foregoing description of the preferred embodiments should be taken by way of illustration rather than by way of limitation of the invention as defined by the claims.

CROSS REFERENCE TO RELATED APPLICATIONS

The present application claims priority and benefit of U.S. Provisional Patent Application 60/012,241, Filed Feb. 26, 1996 and of U.S. Provisional Patent Application 60/011,720 Filed Feb. 15, 1996, the disclosures of which are hereby incorporated by reference herein.

The following PCT applications, each of which names Biosense, Inc as an applicant are also incorporated by reference herein: Catheter Based Surgery filed on or about Feb. 14, 1997 in the Israeli Receiving Office; Intrabody Energy Focusing filed on or about Feb. 14, 1997 in the Israeli Receiving Office; Locatable Biopsy Needle, filed on or about Feb. 14, 1997 in the Israeli Receiving Office; Catheter Calibration and Usage Monitoring filed on or about Feb. 14, 1997 in the Israeli Receiving Office; Precise Position Determination of Endoscopes filed on or about Feb. 14, 1997 in the Israeli Receiving Office; Medical Probes with Field Transducers filed Feb. 14, 1997 in the United States Receiving Office; Catheter with Lumen filed Feb. 14, 1997 in the United States Receiving Office; Movable Transmit or Receive Coils for Location System filed Feb. 14, 1997 in the United States Receiving Office; and Medical Procedures and Apparatus Using Intrabody Probes filed Feb. 14, 1997 in the United States Receiving Office. The PCT application entitled, Multi-Element Energy Focusing, filed Feb. 14, 1996 in the Israeli Receiving Office and naming Victor Spivak as applicant is also incorporated by reference herein.

INDUSTRIAL APPLICABILITY

The invention can be used in medical and related procedures.

What is claimed is:

1. A system for determining the disposition of a probe within the body of a patient, comprising:
   (a) a probe having one or more probe field transducers mounted thereon;
   (b) a plurality of reference field transducers independently movable with respect to one another and locatable in desired, customizable positions with respect to the body of the patient;
   (c) calibration means for determining the relative dispositions of said one or more probe field transducers with respect to one another while said reference field transducers are located in their desired positions;
   (d) transmission means to actuate said reference field transducers and said one or more probe field transducers to transmit one or more non-ionizing fields and detect the transmitted field, so that each such field is transmitted by one element of a transmitter-receiver pair including a reference field transducer and a probe field transducer, and detected by the other element of such pair; and
   (e) calculation means to determine the relative disposition of the probe with respect to said reference field transducers from properties of the detected fields and from the relative dispositions of said reference field transducers with respect to one another.

2. A system as claimed in claim 1, wherein said calibration means and said calculation means are operative to predetermine dispositions of said reference field transducers which have changed relative to one another and to predetermine the disposition of said probe based on said predetermined dispositions of said reference field transducers.

3. A system as claimed in claim 1, wherein said plurality of reference field transducers are mechanically unattached to one another.

4. A system as claimed in claim 1, wherein said plurality of reference field transducers are flexibly connected to one another so as to allow each of said reference field transducers to move independently of one another.

5. A system as claimed in claim 1, wherein said transmission means are operative to transmit the fields from said reference field transducers and including detection means to detect the transmitted fields by means of one or more said probe field transducers.

6. A system as claimed in claim 1, wherein said transmission means are operative to transmit the fields from one or more said probe field transducers and including detection means to detect the transmitted fields by means of said reference field transducers.

7. A system as claimed in claim 1, further comprising means to translate the disposition of said probe relative to said reference field transducers to a known disposition relative to the body of the patient.

8. A system as claimed in claim 7, further comprising an image representing a portion of the patient and display means to display the disposition of the probe in superposition with the image representing a portion of the patient.

9. A system as claimed in claim 8, further comprising a frame of reference of the reference field transducers and said image and means for maintaining registration between the frame of reference of the reference field transducers and said image despite changes in the disposition of said reference field transducers relative to the body of the patient.

10. A system as claimed in claim 1, wherein said calibration means comprise one or more calibration field transducers attached to at least one of said reference field transducers and said calibration means determine the relative dispositions of said reference field transducers with respect to one another by detecting non-ionizing fields transmitted to or from said calibration field transducers.

11. A system as claimed in claim 1, wherein said reference field transducers are provided in a plurality of reference assemblies each including one said reference field transducer and said calibration means comprise one or more calibration field transducers provided in a known, fixed arrangement, said calibration means being operative to determine the relative positions of said reference field transducers with respect to said fixed arrangement by detecting non-ionizing fields transmitted between said one or more calibration field transducers and one or more reference assemblies.

12. A system as claimed in claim 11, wherein said calibration means is operative to determine said dispositions of said reference field transducers relative to said fixed arrangement by detecting fields transmitted between said reference field transducers and said calibration field transducers.

13. A system as claimed in claim 1, further comprising means for securing said reference field transducers to the body of the patient.

14. A system as claimed in claim 1, further comprising means for mounting said reference field transducers in close proximity to the body of the patient.

15. A system as claimed in claim 1, wherein said reference field transducers are repositionable and said calibration means are operative to recalibrate the relative dispositions of the field transducers with respect to one another after said reference field transducers are repositioned.

16. A system as claimed in claim 1, wherein said reference field transducers comprise disposable materials such that said reference transducers are disposable after use.

17. A system as claimed in claim 1, wherein said reference field transducers are carried on a support constructed and arranged to allow independent movement of said reference field transducers.

18. A system as claimed in claim 17, wherein said support includes a plurality of flexible arms to which said reference field transducers are mounted.

19. A system as claimed in claim 17, wherein said support comprises a flexible, sheet-like covering for carrying said reference field transducers thereon.

20. A method for determining the disposition of a probe within the body of a patient, comprising the steps of:
 (a) providing a probe having one or more probe field transducers mounted thereon;
 (b) positioning a plurality of reference field transducers independently with respect to one another in desired, customizable positions with respect to the body of the patient;
 (c) determining the relative dispositions of said reference field transducers with respect to one another while said reference field transducers are located in their desired positions;
 (d) transmitting one or more non-ionizing fields between said probe field transducers and said reference field transducers and detecting each such transmitted field so that each such field is transmitted by one element of a transmitter-receiver pair including a reference field transducer and a probe field transducer, and detected by the other element of such pair; and
 (e) determining the relative disposition of the probe with respect to said reference field transducers from properties of the detected fields and from the relative dispositions of said reference field transducers with respect to one another.

21. A method as claimed in claim 20, further comprising the step of repeating said steps (c) through (e) so as to redetermine dispositions of said reference field transducers which have changed relative to one another and to redetermine the disposition of said probe based on said updated dispositions of said reference field transducers.

22. A method as claimed in claim 20, wherein transmission step comprises transmitting the fields from said reference field transducers and said detection step comprises detecting the transmitted fields by means of one or more said probe field transducers.

23. A method as claimed in claim 20, wherein said transmission step comprises transmitting the fields from one or more said probe field transducers and said detection step comprises detecting the transmitted fields by means of said reference field transducers.

24. A method as claimed in claim 20, further comprising the step of translating the disposition of said probe relative to said reference field transducers to a known disposition relative to the body of the patient.

25. A method as claimed in claim 24, further comprising the step of updating the relative disposition of said probe relative to the body of the patient where the disposition of said reference field transducers have changed relative to the body of the patient.

26. A method as claimed in claim 24, further comprising using an image representing a portion of the patient and further comprising the step of displaying the disposition of the probe in superposition with the image representing a portion of the patient.

27. A method as claimed in claim 20, wherein said step of determining the relative positions of said reference field transducers comprises the step of attaching one or more calibration field transducers to at least one of said reference field transducers and determining the relative positions of said reference field transducers with respect to one another by detecting non-ionizing fields transmitted between said calibration field transducers and said reference field transducers.

28. A method as claimed in claim 20, wherein said step of determining the relative positions of said reference field transducers comprises providing one or more calibration field transducers provided in a known, fixed arrangement and determining the relative positions of said reference field transducers with respect to one another by detecting non-ionizing fields transmitted between said one or more calibration field transducers and said reference field transducers.

29. A method as claimed in claim 20, further comprising the step of securing said reference field transducers to the body of the patient.

30. A method as claimed in claim 20, further comprising the step of locating said reference field transducers in close proximity to the body of the patient.

31. A method as claimed in claim 20, further comprising the step of disposing of said reference field transducers after use.

* * * * *